(12) United States Patent
Den Ouden

(10) Patent No.: US 6,334,257 B1
(45) Date of Patent: Jan. 1, 2002

(54) ELECTRONIC ANGLE-MEASURING DEVICE

(75) Inventor: Arie Huibrecht Den Ouden, St. Annaland (NL)

(73) Assignee: Erasmus Universiteit Rotterdam Instituut Revalidatiegeneeskunde Van de Faculteit Geneeskunde-en Gezondheidswetenschappen, Rotterdam (NL)

( * ) Notice: Subject to any disclaimer, the term of this patent is extended or adjusted under 35 U.S.C. 154(b) by 0 days.

(21) Appl. No.: 09/424,952

(22) PCT Filed: Jun. 5, 1998

(86) PCT No.: PCT/NL98/00332

§ 371 Date: Mar. 2, 2000

§ 102(e) Date: Mar. 2, 2000

(87) PCT Pub. No.: WO98/55829

PCT Pub. Date: Dec. 10, 1998

(30) Foreign Application Priority Data

Jun. 5, 1997 (NL) ............................................... 1006240

(51) Int. Cl.$^7$ ................................................. G01B 3/56
(52) U.S. Cl. ............................... 33/1 N; 33/534; 33/538
(58) Field of Search ........................... 33/1 N, 534, 538, 33/1 PT, 456, 471, 512

(56) References Cited

U.S. PATENT DOCUMENTS

| | | | |
|---|---|---|---|
| 3,815,247 A | | 6/1974 | Debrunner |
| 3,952,417 A | | 4/1976 | Bestehorn |
| 4,513,512 A | * | 4/1985 | Fischer ........................ 33/1 N |
| 5,163,228 A | | 11/1992 | Edwards et al. |
| 5,392,526 A | * | 2/1995 | Sprague et al. ............... 33/1 N |
| 5,603,236 A | * | 2/1997 | Hongo ......................... 33/1 N |

FOREIGN PATENT DOCUMENTS

| | | |
|---|---|---|
| DE | 35 42 943 | 6/1987 |
| EP | 0 189 721 | 8/1986 |
| EP | 0 287 149 | 10/1988 |
| GB | 2 008 287 | 5/1979 |

* cited by examiner

*Primary Examiner*—Andrew H. Hirshfeld
(74) *Attorney, Agent, or Firm*—Young & Thompson

(57) ABSTRACT

Electronic angle-measuring device with two legs which are pivotably attached to one another. An angle-measuring sensor having two measurement plates which can be displaced with respect to one another is situated in the pivot point of these legs. At the end which is remote form the pivot point, the legs are provided with a sensor part which is pivotably attached thereto and is connected, via a cord connection, to the measurement plates of the sensor.

13 Claims, 4 Drawing Sheets

ELECTRONIC ANGLE-MEASURING DEVICE

BACKGROUND OF THE INVENTION

The present invention relates to an angle-measuring device in accordance with the preamble of claim 1.

DESCRIPTION OF THE RELATED ART

An angle-measuring device of this kind is known from American patent U.S. Pat. No. 3,952,417, in which the sensor parts are each connected to the central part via two legs. These two always form a type of parallelogram structure, in which one leg of one sensor part is pivotably connected to one leg of the other sensor part.

For medical purposes, it is often important to know the pivoting movement of two body parts with respect to one another. Obviously, it is also important for other purposes to know the angle between two parts.

However, there are often obstacles which make it impossible to place the two legs flat against the body parts or other parts to be measured in question.

European Patent Application 0,287,149 proposes a solution to this problem in that the legs are no longer pivotably connected to one another, but rather are attached to one another by means of a flexible strip. Sensitive parts are situated in this strip, and it is possible to use this strip when it does not bear against the body parts or other parts to be measured in question. In this way, obstacles situated in the region of the vertex are circumvented.

The device which is described in European Application 0.287,149 is particularly complicated, and it has been found that after a relatively long period of time it is no longer possible to ensure that the device is sufficiently accurate. Moreover, it is particularly sensitive to damage.

A number of the problems indicated above can be solved using the angle gauge in accordance with American patent U.S. Pat. 3,952,417. However, the travel of this gause, i.e. the angular range which can be measured, is limited. Moreover, this design is complicated and fragile as a result of the use of four external legs.

British patent 2,008,287 has disclosed a loading/unloading arm provided with sensors for determining the angle of the various arm parts. In this patent, one part of the angle-measuring device is permanently fixedly connected to the surrounding area. An angle-measuring sensor is arranged on each of the pivoting arms, at a distance from the pivot point.

SUMMARY OF THE PRESENT INVENTION

The object of the present invention is to provide an angle-measuring device with which a wide range of angles can be covered and which has a comparatively simple design.

This object is achieved in the case of an angle-measuring device as described below.

The fact that the pivot point of the legs coincides with the pivot point of the measurement means results in a considerable structural freedom, with the result that it is possible to design the angle-measuring device in such a manner that a large angle range can be covered.

The movement of the sensor parts can be transmitted in any manner which is known in the prior art. An example which may be mentioned is a mechanical connection, such as a chord connection between the sensor parts and the sensor plate or plates in the event of using a single angle-measuring sensor, In a preferred embodiment, this connection is situated in the pivot point of the two legs which is described above.

It will be understood that instead of the chord connection mentioned here it is possible to use any other connection which is known in the prior art.

Any design which is known in the prior art may be used for the sensor described above. For example, it is possible to use resistance-based sensor plates which transmit a different resistance value on rotation (potentiometer). It is also possible to use a series of light-sensitive diodes and a light source.

However, it is preferred to design the angle-measuring sensor as a capacitative sensor. In this case, the plates of the sensor act as a condenser plate.

It is possible to accommodate at least some of the associated electronics in the housing which is arranged in the region of the pivot point of the two legs. Obviously, it is also possible to arrange another part of the electronics outside the electronic angle-measuring device according to the invention and to provide a wireless connection or a connection with a wire to a device of this kind.

It will be understood that the angle gauge described above has numerous applications both in the medical field and in other fields. In addition to measuring angles, the electronic design of this device makes it particularly easy to calculate radii of curvature and, from this, to determine circumferences and surface areas.

BRIEF DESCRIPTION OF THE DRAWINGS

The invention will be explained below with reference to an exemplary embodiment which is illustrated in the drawing in which.

DESCRIPTION OF THE PREFERRED EMBODIMENTS

Figure 1:
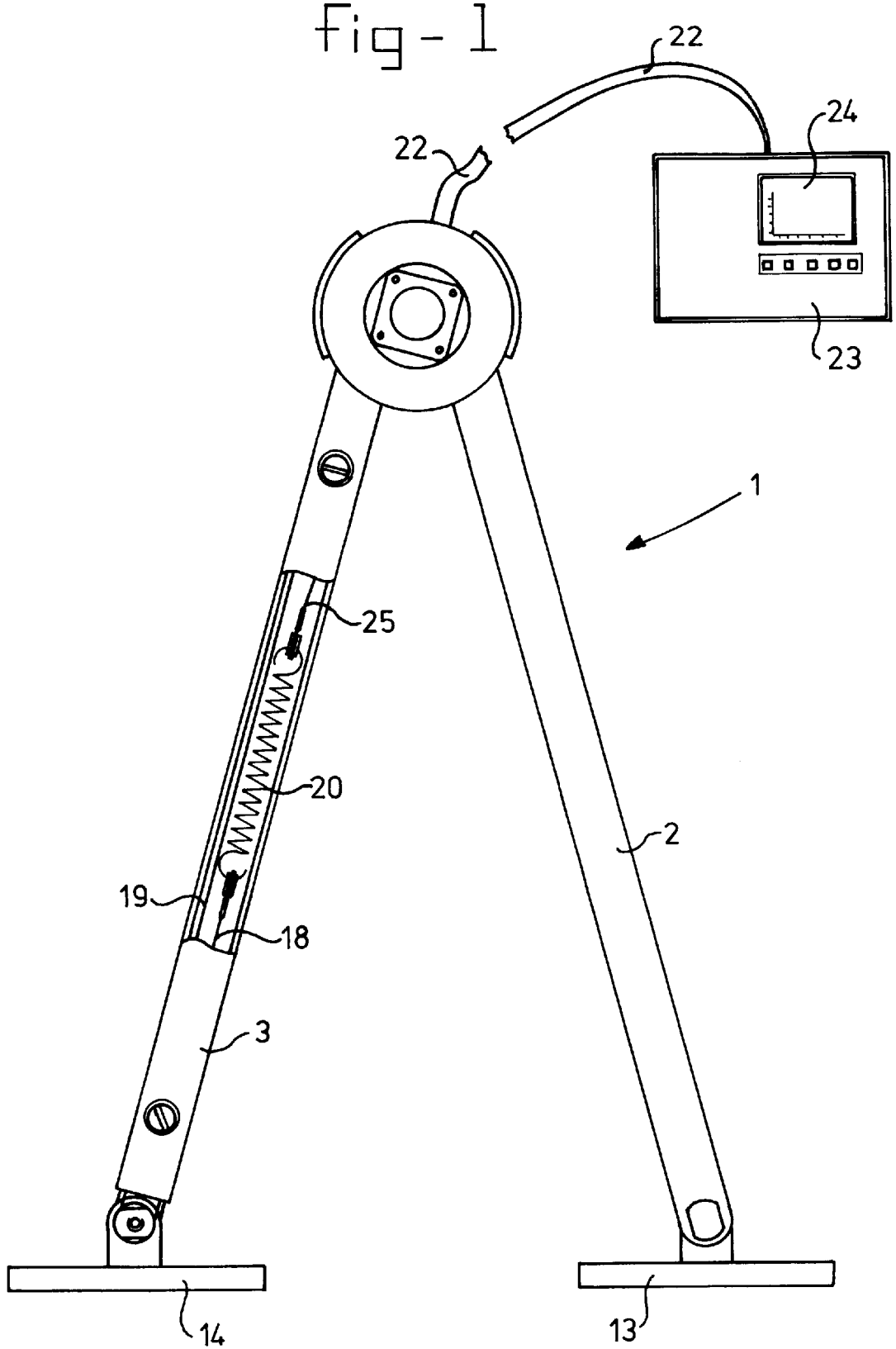
FIG. 1 shows a front view of the electronic angle-measuring device according to the present invention which is coupled to a read-out box.
Figure 2:
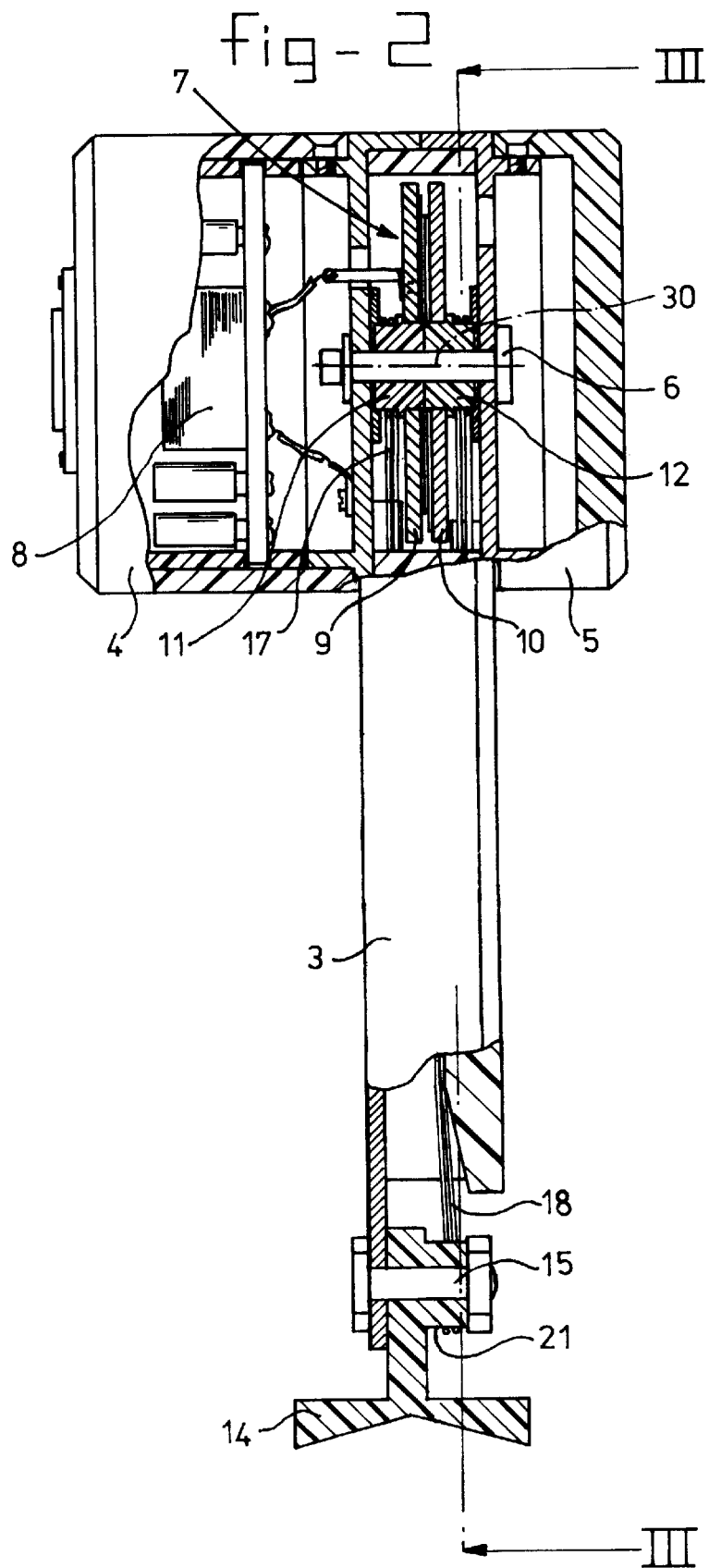
FIG. 2 shows a side view, partially in cross-section, of the device in accordance with FIG. 1.

In the figures, the measuring device according to the present invention is denoted overall by 1. This device has two legs which are denoted by 2 and 3, respectively, As can be seen from FIG. 1 and, in particular FIG. 2, leg 3 is connected to cover cap 4 and leg 2 is connected to cover cap 5. These cover caps can move past One another and provide a dustproof housing in which a sensor 7 is arranged. Legs 2 and 3 rotate about a pivot pin 6, the axis of which is Indicated by 30. Sensor 7 is connected to electronics 8 situated in cover cap 4, and the signal transmitted by this electronic system is fed via a cable 22 to a read-out box 23 which is provided with a read-out window 24.

Sensor 7 is provided with two sensor plates 9, 10. In this case, the sensor is a capacitative sensor, so that the position of the condensor plates 9, 10 with respect to one another determines the capacitance of sensor 7, thus providing a measurement of the angle. It will be understood that the sensor may comprise any other sensor which is known from the prior art and which is designed without these plates or with other types of plates.

Figure 3:
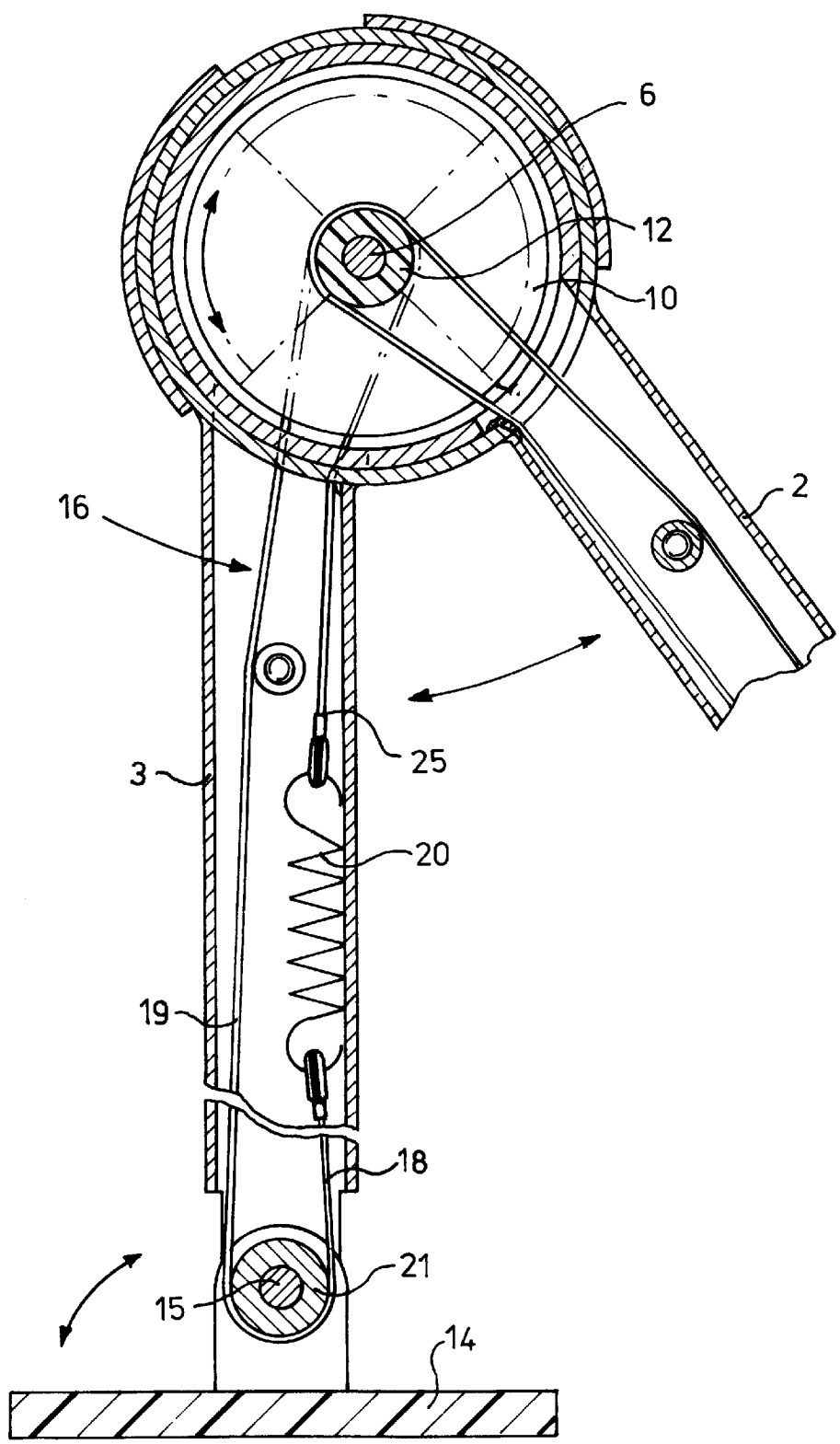
FIG. 3 shows a partially cut-away view of the device in accordance with FIG. 1, in order to explain how the chords run.

In the region of their free ends, the legs 2, 3 are provided with sensor parts 13, 14. These are connected, via a pivot pin 15, to the legs in question. The sensor parts are each provided with an annular part 21 which acts as a pulley 11 and 12, respectively, coupled to sensor plates 9 and 10, respectively. Chord 16 extends through the interior of the leg in question, details of this chord can be seen from FIG. 3. It can be seen from this figure that a first chord part 18 extends towards annular part 21, a second chord part 19 extends towards the sensor plate in question and a third chord part 25 extends between the pulley of the sensor plate in question and a spring 20 which tensions of the said first chord part 18.

The sensor plates or pulleys 11, 12 are not connected to the legs 2, 3 and their rotation about pivot pin 6 is controlled exclusively by movement of the chord in question. This means that if, in the stationary position of leg 3, sensor part 14 is moved to and fro, the associated pulley also moves to and fro. If leg 3 is moved and sensor part 14 is not in contact, the sensor part 14 will move with it. Naturally, in the event of this movement the associated pulley on the sensor will also rotate.

Surprisingly it has been found that in this way it is possible to determine the angle which the sensor parts 13, 14 form with respect to one another, which is the angle to be measured, particularly accurately.

Figure 4:
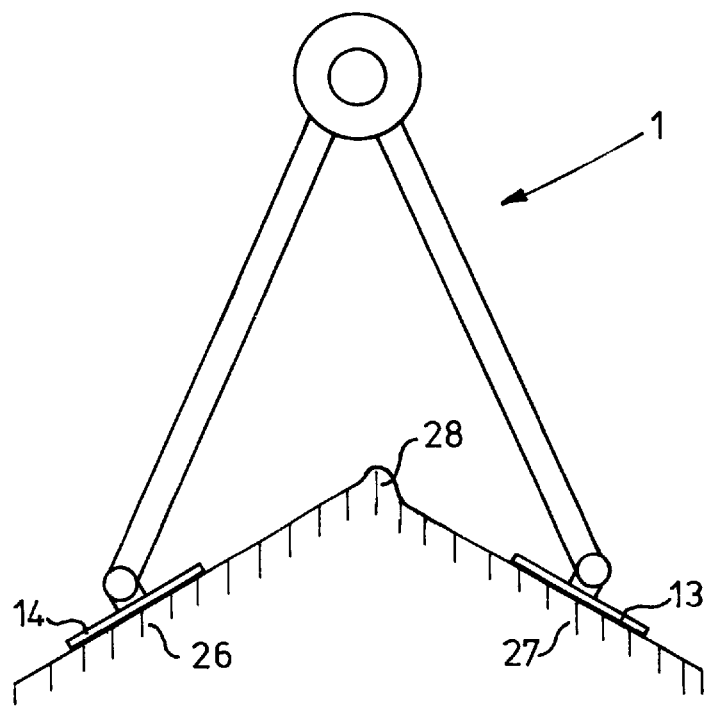
FIG. 4 shows how to measure the angle between two different parts, as a first example.

FIG. 4 shows an example in which the angle between two surfaces 26 and 27 is to be determined, but where surface 26 is provided with a projection 28. As a result, It is impossible to use conventional angle-measuring devices in which the legs 2, 3 would be placed along surfaces 26, 27, since the reading from surface 27 would be inadequate. With the design proposed here this does not represent any problem, since the sensor parts 13, 14 are placed beyond the projection 28.

Figure 5:
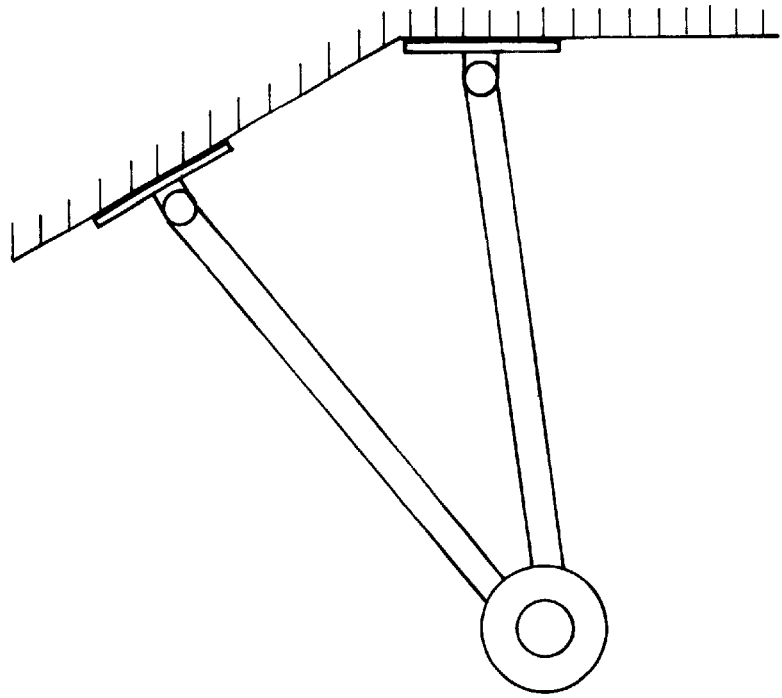
FIG. 5 shows how to measure the angle between two parts as a second example.

The same applies to the design shown in FIG. 5. When measuring under these conditions, the size of the cover caps 4, 5 would impede accurate results if measurement were carried out exclusively using legs 2, 3.

It is clear from the above that numerous variants are possible in the measurement and that the "most impossible" positions can be adopted with the device according to the invention. The above-described electronic angle-measuring device can be used both in the medical field and in other fields. The design shown here is particularly robust, owing to the fact that the fragile chord part is mostly situated within the legs 2, 3 and the cover caps. Elongation of the chords is absorbed by spring 20.

It would be understood by the person skilled in the art that numerous variants on that which is shown here are possible. For example it is possible to use bars, toothed belts, toothed wheels and the like. Designs of this nature are obvious to the person skilled in the art on reading the above description and lie within the scope of the appended claims.

What is claimed is:

1. Angle-measuring device (1) comprising:
   two legs (2,3) which are pivotably attached to one another at a pivot point,
   each of the two legs (2, 3) being provided at a free end with a sensor part (13, 14) which is pivotably connected therewith;
   angle-measuring means being arranged in the region of the pivot point for determining the pivot angle of the sensor parts relative to each other (6),
   which angle-measuring means comprise two measuring parts (9, 10) which can rotate with respect to one another about an axis (30),
   wherein said angle-measuring means comprises an electrical sensor (7), and each of said legs (2, 3) pivot about said axis (30),
   each of the two measuring parts (9, 10) of the angle measuring means is connected to a respective one of said sensor parts via a mechanical connection,
   said mechanical connections each comprise a cord connection (16, 17), and the sensor part pivotably connected with each leg and the angle-measuring means are provided with a pulley.

2. Angle-measuring device according to claim 1, in which said angle-measuring means comprises a capacitative sensor.

3. Electronic angle-measuring device comprising:
   two legs which are pivotably attached to one another about an axis,
   each leg being provided at its free end with a sensor part freely pivotably connected thereto;
   angle-measuring means for determining the pivot angle of the sensor parts relative to each other comprising an electrical sensor, being arranged in the region of a pivot point of the axis, which angle-measuring means comprise two measuring parts which can rotate with respect to one another about said axis;
   a transfer means for transferring a pivot angle of each of said sensor parts to said angle-measuring means.

4. Angle-measuring device according to claim 3, wherein said transfer means for transferring said pivot angle of each of said sensor parts to said angle measuring means comprises a mechanical connection between each said measuring part and a respective one of said sensor parts.

5. Angle-measuring device according to claim 4, in which the said mechanical connections each comprise a cord connection (16, 17).

6. Angle-measuring device according to claim 5, in which the mechanical connections each comprise a pulley.

7. Angle-measuring device according to claim 6, in which the said angle-measuring means comprises a capacitative sensor.

8. An electronic angle-measuring device, comprising:
   two legs pivotably connected to one another about an axis;
   an electronic angle-measuring sensor provided with two parts that rotate with respect to one another about the axis and whose position with respect to one another provides an angle measurement;
   a sensor part freely pivotably connected at a free end of each of the two legs; and an angle transfer arrangement operatively connected between each sensor part and the angle-measuring sensor to transfer a pivot angle of each sensor part to the angle-measuring sensor.

9. The electronic-angle measuring device of claim 8, wherein,
   the angle transfer arrangement comprises a mechanical connection that can transfer the pivot angle of each sensor part to the angle-measuring sensor.

10. The electronic-angle measuring device of claim 8, wherein, the angle-measuring sensor comprises a capacitive sensor.

11. The electronic-angle measuring device of claim 8, wherein,
    the angle transfer arrangement comprises two pulley and cord assemblies, a first of the two assemblies connecting the angle-measuring sensor and the sensor part pivotably connected with a first of the two legs, and a second of the two assemblies connecting the angle-measuring sensor and the sensor part pivotably connected with a second of the two legs.

12. The electronic-angle measuring device of claim 11, wherein, the pulley of the first of the two assemblies is connected to one of the two parts of the angle-measuring sensor, and the pulley of the second of the two assemblies is connected to the other of the two parts of the angle-measuring sensor.

13. The electronic-angle measuring device of claim 12, wherein, the pulley of the first of the two assemblies is connected to the sensor part of the first of the two legs, and the pulley of the second of the two assemblies is connected to the sensor part of the second of the two legs.

* * * * *